(12) United States Patent
Drury

(10) Patent No.: US 9,068,968 B2
(45) Date of Patent: Jun. 30, 2015

(54) URINE ANALYSIS DEVICE, METHOD AND SYSTEM

(71) Applicant: Daniel Gordon Drury, Camp Hill, PA (US)

(72) Inventor: Daniel Gordon Drury, Camp Hill, PA (US)

( * ) Notice: Subject to any disclaimer, the term of this patent is extended or adjusted under 35 U.S.C. 154(b) by 122 days.

(21) Appl. No.: 13/933,791

(22) Filed: Jul. 2, 2013

(65) Prior Publication Data
US 2015/0009502 A1   Jan. 8, 2015

(51) Int. Cl.
  *G01J 3/52* (2006.01)
  *G01N 33/493* (2006.01)
  *G01N 33/52* (2006.01)
  *G01N 21/85* (2006.01)

(52) U.S. Cl.
  CPC ............ *G01N 33/493* (2013.01); *G01J 3/52* (2013.01); *G01N 33/52* (2013.01); *G01N 21/85* (2013.01)

(58) Field of Classification Search
  USPC .................................... 356/402–425
  See application file for complete search history.

(56) References Cited

U.S. PATENT DOCUMENTS

| | | |
|---|---|---|
| 1,806,806 A | 5/1931 | Kocour |
| 1,868,542 A | 7/1932 | Pennington |
| 3,176,577 A | 4/1965 | Frank |
| 3,381,572 A | 5/1968 | Tuwiner |
| 4,523,852 A | 6/1985 | Bauer |
| 4,871,258 A | 10/1989 | Herpichboehm et al. |
| 4,877,580 A | 10/1989 | Aronowitz et al. |
| 4,943,416 A | 7/1990 | Kikuchi et al. |
| 5,137,692 A | 8/1992 | Fritz |
| 5,182,707 A | 1/1993 | Cooper et al. |
| 5,184,359 A | 2/1993 | Tsukamura et al. |
| 5,231,576 A | 7/1993 | Suzuki et al. |
| 5,724,148 A | 3/1998 | Howard, III et al. |
| 5,877,028 A | 3/1999 | Chandler et al. |
| 6,156,272 A | 12/2000 | Lee et al. |
| 6,403,298 B1 | 6/2002 | Lee et al. |
| 6,673,630 B2 | 1/2004 | Albarella et al. |
| 6,750,007 B2 | 6/2004 | Canter et al. |
| 7,148,070 B2 | 12/2006 | Minter |
| 7,247,493 B2 | 7/2007 | Kopelman |
| 2006/0232059 A1 | 10/2006 | Fortune et al. |
| 2007/0048224 A1 * | 3/2007 | Howell et al. ............. 424/9.1 |
| 2008/0050451 A1 | 2/2008 | Mabry |
| 2008/0274495 A1 | 11/2008 | Jumonville et al. |

OTHER PUBLICATIONS

Y&R Sao Paulo, Bonafort Water: "Sticker" Promo / PR Ad, released Mar. 2011. Retrieved from Internet on Sep. 19, 2013: <URL: http://www.coloribus.com/adsarchive/promo-casestudy/bonafort-water-sticker-16584055>.

Armstrong, Lawrence E., HydrationCheck, 2011 [website], [retrieved on Jul. 1, 2013]. Retrieved from the Internet: <URL: http://www.hydrationcheck.com/products.php>.

* cited by examiner

*Primary Examiner* — Abdullahi Nur
(74) *Attorney, Agent, or Firm* — Buchanan Ingersoll & Rooney PC

(57) ABSTRACT

A device, method and system are provided for analyzing urine color to determine the hydration level of an individual. The device is nonabsorbent and includes a water-resistant adhesive configured to adhere the device to a urine receptacle such as a urinal or toilet. The device includes a color scale possessing a plurality of shades of yellow arranged from lightest to darkest. Each shade of yellow corresponds to a hydration level. The device allows the individual to assess their hydration level while simultaneously urinating into the urine receptacle.

20 Claims, 7 Drawing Sheets

URINE ANALYSIS DEVICE, METHOD AND SYSTEM

TECHNICAL FIELD

The present invention relates to a device, method and system for determining the hydration level of an individual based on urine color.

BACKGROUND

Although dehydration is commonly viewed as a condition affecting athletes and manual laborers, dehydration is a health concern for all individuals. Dehydration is especially a concern in places where individuals are susceptible to developing a fluid imbalance and/or thermoregulatory challenge, like for example, in senior centers, public schools, hospitals and national parks.

The hypothalamus inside the brain monitors body temperature, and when heat begins to accumulate, certain physiological adjustments are made to maintain a healthy body temperature. Regulation of body temperature is accomplished in a variety of ways including radiation, convection, conduction and evaporation through sweating. Evaporation is a primary mode of heat transfer during physical exertion and can account for up to 80% of the body's heat loss. In extremely hot conditions, the human body can lose as much as 2 liters of sweat per hour. If the body's water supply is not replenished continuously, dehydration might occur. In some cases, this can result in dangerous and potentially life-threatening consequences.

A variety of factors affect an individual's sweat rate. These factors include the ambient temperature and humidity, the intensity and duration of the physical exertion, the type of clothing worn by the individual, the individual's fitness level, hereditary factors, and additionally the individual's state of acclimatization and current hydration status. Early warning signs that an individual is entering a state of dehydration include: irritability, vomiting, thirst, headache, dizziness, fatigue, chills and darker urine than normal. If allowed to persist, dehydration can lead to muscle cramps, excessive sweating, heat exhaustion and possibly heat stroke.

An individual's desire to consume fluids (i.e., thirst) is oftentimes not an accurate means by which to gauge the individual's hydration level. The hypothalamus monitors the body's temperature and controls the physiological response to a thermoregulatory challenge. The hypothalamus is affected by sodium levels, blood osmolality and overall plasma volume. The mechanisms for controlling body temperature are hormonal, physiological, metabolic and behavioral. All of these factors are subject to individual variation, and therefore it can be difficult to predict the exact amount of fluid an individual should consume to avoid dehydration.

Clinical methods to monitor and diagnose dehydration include tests based on plasma osmolality, urine specific gravity, urine osmolality and various isotope techniques. Field methods for diagnosing dehydration are generally less accurate than clinical methods, but nonetheless provide valuable indicators of dehydration. Field methods include monitoring acute weight loss (e.g., pre-practice vs. post-practice weight), urine color and other typical signs of dehydration (e.g., thirst, dizziness, headache, irritability etc.).

Urine color can be used to assess an individual's hydration level because urine color may change in response to changes in the individual's overall hydration level. A euhydrated individual typically produces urine which is light yellow or straw color. A dehydrated individual produces urine that is dark yellow, orange, gold, light brown or brownish-green. When the body enters a state of dehydration, there is a deficit between fluid intake and fluid loss. This deficit is reflected by an increased concentration of particulates excreted in the urine. If more water is lost through sweating than is consumed through drinking, less water is available to dilute the particulates in the urine, and so the urine color becomes darker.

Known color scales for analyzing urine color are printed on a paper chart. An individual must collect his or her urine in a clear container, and then hold the paper chart next to the urine sample to make the color comparison. Individuals oftentimes object to the collection and handling of urine that is required to obtain an accurate measurement. This process is also time consuming in that the urine must first be collected in the clear container, and subsequently compared to the paper chart. Because known color scales require the collection of urine, these color scales are not helpful to an individual who excretes his or her urine into a urinal or toilet. A need therefore exists for a quicker and less burdensome manner of analyzing urine color.

SUMMARY

A nonabsorbent urine analysis device for determining the hydration level of an individual based on urine color is disclosed. The nonabsorbent urine analysis device can be adhered to a urine receptacle. The nonabsorbent urine analysis device includes a base, a color scale, a plurality of hydration level indicators and a water-resistant adhesive. The base possesses a front side and a back side. The color scale is applied to the front side of the base, and includes a plurality of shades of yellow arranged from lightest to darkest. Each shade of yellow corresponds to a hydration level. The water-resistant adhesive is applied to the back side of the base, and is configured to adhere the base to the urine receptacle.

Also disclosed is a method for determining a hydration level based on urine color. The method includes applying a stream of urine to a water-resistant color scale adhered to a urine receptacle so that the urine flows over the water-resistant color scale. The method includes visually comparing the urine color to a plurality of colors included on the water-resistant color scale while the urine flows over the water-resistant color scale. The method additionally involves identifying a color included on the water-resistant color scale which most closely matches the urine color, and determining the hydration level by referencing a hydration level indicator corresponding to the identified color.

Also described herein is a urine analysis system including a urinal, a first color scale, a water-resistant adhesive and a second color scale. The urinal includes a urine reception surface. The first color scale is adhered to the urine reception surface by a water-resistant adhesive. The first color scale is water-resistant and includes a plurality of shades of yellow arranged from lightest to darkest. The second color scale is positioned exteriorly of the urinal and includes a plurality of shades of yellow arranged from lightest to darkest. The second color scale also includes a plurality of hydration level indicators positioned adjacent to and/or overlapping at least one of the shades of yellow on the second color scale.

BRIEF DESCRIPTION OF THE DRAWINGS

Objects and advantages of the invention will become apparent upon reading the following detailed description of preferred embodiments and upon reference to the drawings, in which.

DETAILED DESCRIPTION OF PREFERRED EMBODIMENTS

The present invention allows an individual to determine their hydration level while simultaneously urinating into a urine receptacle such as a urinal or toilet. A nonabsorbent urine analysis device is adhered to the urine receptacle by a water-resistant adhesive. The device is nonabsorbent in that it does not absorb or chemically react with urine. The nonabsorbent urine analysis device includes a color scale with different colors corresponding to different levels of hydration. While urinating on the nonabsorbent urine analysis device, the individual visually compares the urine color to the color scale. Once the urine color has been matched to the color scale, the individual can refer to a hydration level indicator to determine his or her hydration level. The device can be used by all individuals, including those facing a thermoregulatory challenge due to physical exertion and/or a fluid imbalance.

Figure 1:
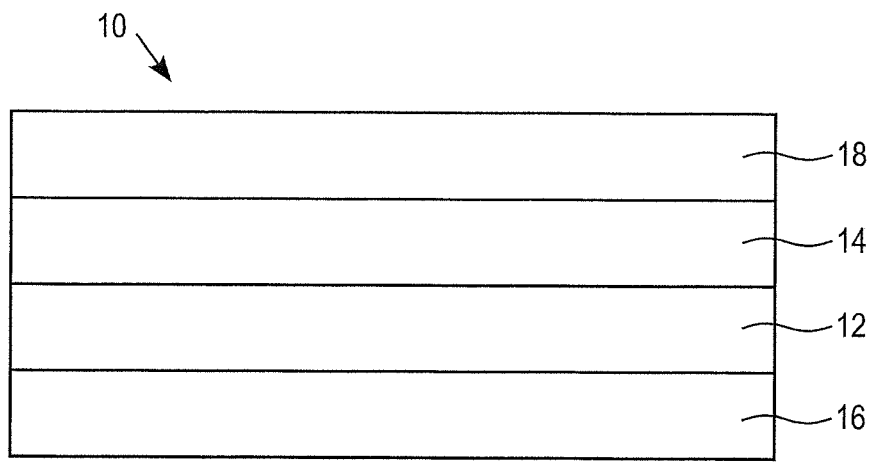
FIG. 1 is a side view of a nonabsorbent urine analysis device according to an embodiment of the present invention.

FIG. 1 illustrates a side view of a nonabsorbent urine analysis device 10. The nonabsorbent urine analysis device 10 includes base 12 that is bordered on opposite sides by a color scale 14 and a water-resistant adhesive 16. The color scale 14 can be formed by printing ink directly on the base 12. The color scale 14 can also be a separate layer of material placed on top of the base 12.

The nonabsorbent urine analysis device 10 is designed to withstand repeated contact with urine and water. The base 12 can be made of plastic so that it does not absorb water. If the base 12 is made of paper or absorbent material, the exposed surfaces of the base can be covered with a water-resistant coating to prevent absorption of urine and/or water. The color scale 14 is also made water-resistant. This is accomplished, for example, by covering the color scale 14 with a water-resistant layer 18 as shown in FIG. 1. The water-resistant layer 18 is transparent so that the color scale 14 is visible to the user. The water-resistant layer 18 can be a layer of clear plastic such as polyvinyl chloride, polyurethane, low density polyethylene, high density polyethylene, polystyrene, polypropylene and/or polyester, or other suitable materials. The water-resistant layer 18 shown in FIG. 1 sits on top of the color scale 14, but may also wrap around the sides of the color scale 14 and/or the base 12.

The water-resistant adhesive 16 bonds the nonabsorbent urine analysis device 10 to the urine receptacle so that the nonabsorbent urine analysis device 10 is held in a fixed position. Water repeatedly flows over the nonabsorbent urine analysis device 10 each time the urinal is flushed. A material is selected for the water-resistant adhesive 16 that can withstand intermittent flows of water. Acrylic adhesives are suitable for this purpose such as the MP690 adhesive sold by Morgan Adhesives Company. The water-resistant adhesive 16 is capable of bonding to materials commonly used to construct a urinal or toilet such as porcelain, steel and/or marble.

The nonabsorbent urine analysis device 10 is bendable so that it can press flushly against a curved surface of the urine receptacle. The nonabsorbent urine analysis device 10 possesses a thickness allowing it to be relatively flexible.

The layers of the nonabsorbent urine analysis device 10 are not limited to those illustrated in FIG. 1. Additional layers may be included depending on durability and cost considerations.

Figure 2:
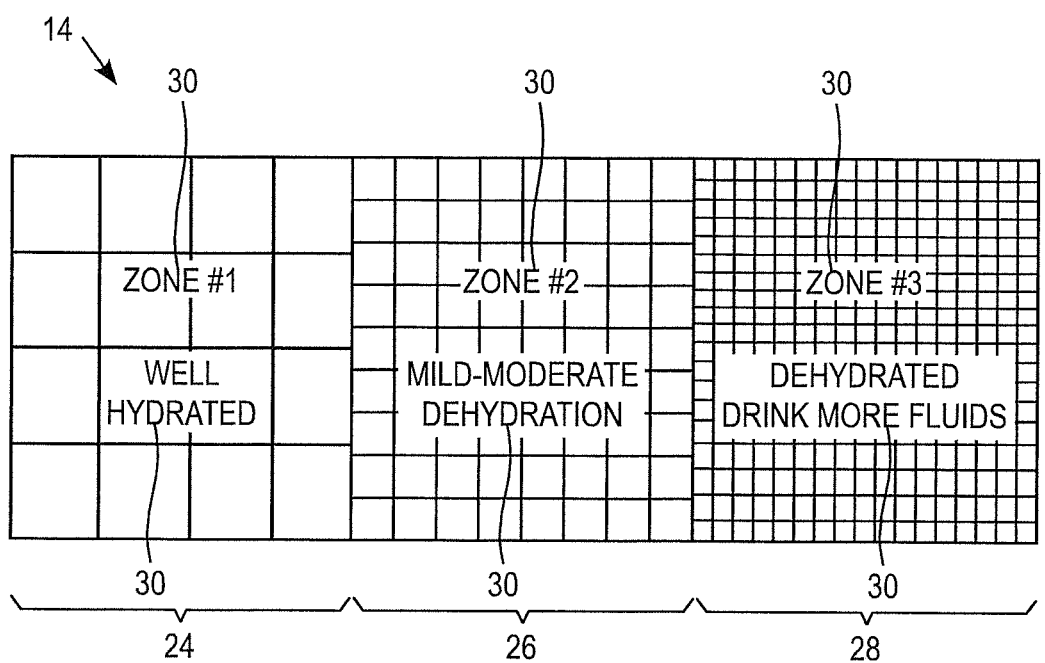
FIG. 2 is a top view of the color scale.

FIG. 2 depicts a front view of the color scale 14. The color scale 14 includes a plurality of colors arranged from lightest to darkest. The darker colors are depicted with denser cross-hatching in FIG. 2. The color scale 14 includes at least three color regions 24, 26 and 28. Each color region 24, 26 and 28 may possess a single color. In one embodiment, the color scale 14 progressively changes from lighter colors to darker colors so that there is not a distinct color transition between each of the color regions 24, 26 and 28. Each color therefore blends into an adjacent color. In such an embodiment, each color region 24, 26 and 28 may include multiple shades of color.

The color scale 14 includes multiple shades of yellow ranging from light yellow to dark yellow. The darker end of the color scale 14 may include shades of orange, gold, light brown, dark brown, and/or brownish-green. In one embodiment, the color scale 14 includes eight colors having the following color values: (1) 17-B1; (2) 9-H1; (3) 17-J1; (4) 17-L1; (5) 9-IS; (6) 9-L3; (7) 12-K6; and (8) 23-L1. These color values refer to the Classic Compendium of Color discussed in Maerz, A. and Paul, M. R., *Dictionary of Color* (2nd Ed.) New York: McGraw-Hill, 1950 at pages 41-69. The color scale 14 may progressively change between these eight colors, or the color scale 14 may include eight distinct color regions with each region possessing a single one of the eight colors. In one embodiment, the color region 24 includes color values 17-B1, 9-H1 and 17-J1; the color region 26 includes color values 17-L1 and 9-IS; and color region 28 includes color values 9-L3, 12-K6 and 23-L1. Each of the color regions 24, 26 and 28 may blend into an adjacent color region, and the colors within each individual color region may blend into each other so that the colors progressively change across the color scale 14.

Each of the color regions 24, 26 and 28 may be separated by a white background. The individual can view the urine flowing over the white background between two adjacent color regions. This may make it easier for the individual to compare the urine color to the color regions 24, 26 and 28. Instead of a white background, empty space may separate each of the color regions 24, 26 and 28. In one embodiment, the white background or empty space may be positioned in the interior of one or more of the color regions 24, 26 and 28 so that the respective color region surrounds the white background or empty space.

Each of the color regions 24, 26 and 28 corresponds to a different level of hydration such as euhydration, mild-moderate dehydration and severe dehydration. Each color region 24, 26 and 28 includes a hydration level indicator 30 that helps the individual determine their hydration level. The hydration level indicators 30 include words, numbers and/or a graphic. The hydration level indicators 30 may be applied or printed directly on the color scale 14 as shown in FIG. 2. The hydration level indicators 30 can also be offset from the color scale 14. The hydration level indicator 30 can simply be a reference number that refers to a chart listing reference numbers and descriptions of their corresponding hydration levels. Each hydration level indicator 30 can also include a written description of the hydration level as shown in FIG. 2. The hydration level indicators 30 can include a graphic such as an image of a thumbs up or a thumbs down.

Figure 3:
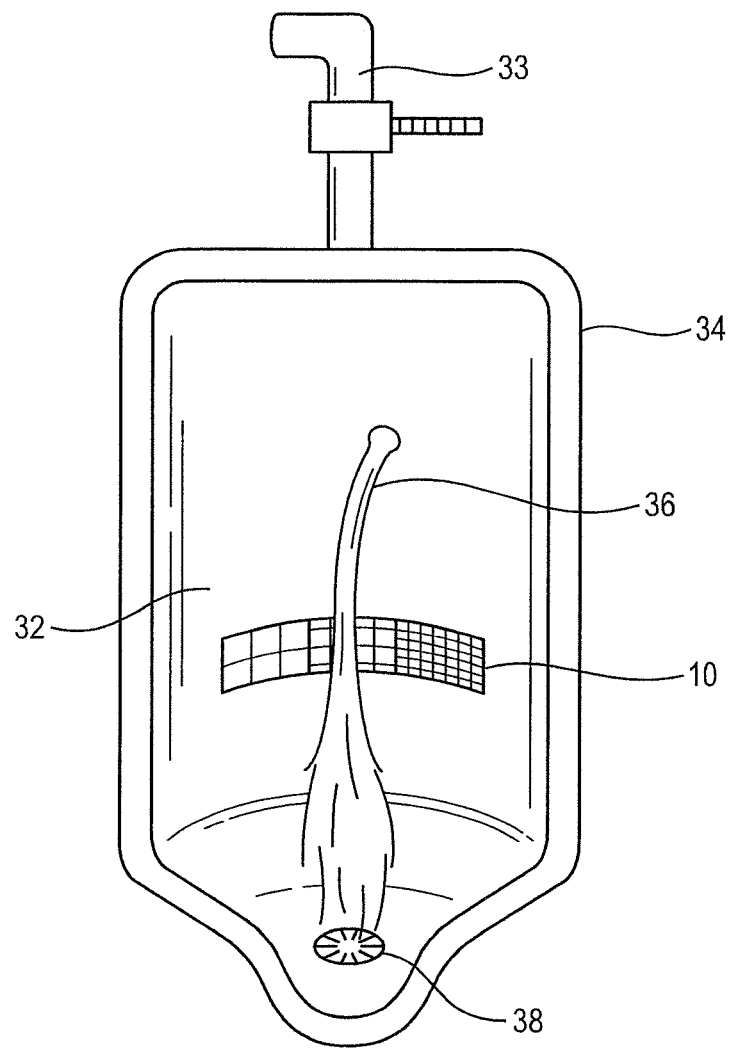
FIG. 3 is a front view of the nonabsorbent urine analysis device applied to a urinal.

A method of determining an individual's hydration level will be described with reference to FIG. 3. This figure illustrates the nonabsorbent urine analysis device 10 adhered to a urine reception surface 32 of a urinal 34. The individual applies a stream of urine 36 to the urine reception surface 32 above the nonabsorbent urine analysis device 10 and/or directly on the nonabsorbent urine analysis device 10. As the urine 36 flows over the nonabsorbent urine analysis device 10, the individual visually compares the urine color to the colors included on the color scale 14. The individual moves the stream of urine 36 so that the urine 36 flows over different portions of the color scale 14. The user visually compares the urine color to the color scale 14 to identify a color on the color scale 14 which most closely matches the urine color. The user then determines the hydration level by referencing the hydration level indicator 30 associated with the identified color. For example, if the urine color matches a color included in the color region 24, the user determines the hydration level by reading the hydration level indicator 30 stating "WELL HYDRATED". The urine flows into a drain 38 after flowing over the nonabsorbent urine analysis device 10. The individual may flush the urinal 32 by operating a plumbing fixture 33 attached to the top of the urinal 32 after the individual is finished urinating. The plumbing fixture 33 opens a valve that allows water to flow over the urine reception surface 32 and into the drain 38.

The above-described method does not require the individual to collect or handle the urine any differently than he or she would during a normal voiding process. Sanitary concerns are therefore less likely to discourage individuals from using the nonabsorbent urine analysis device 10. The urine color can be assessed during the normal voiding process, and so there is no additional time burden placed on the individual to determine his or her hydration level. The relative quickness of the hydration level determination benefits individuals performing physically strenuous tasks under time constraints, such as members of the military, firefighters, manual laborers and athletes.

In may be difficult for some individuals to read the hydration level indicators 30 included on the nonabsorbent urine analysis device 10 while urinating. Other individuals may not understand how to use the nonabsorbent urine analysis device 10 to assess their hydration level. One way to address these issues is to place a placard 40 including a second color scale 42 on the wall above the urinal 34. The placard 40 may be positioned at eye-level so that the individual has an unobstructed view of the placard 40 while urinating.

Figure 4:
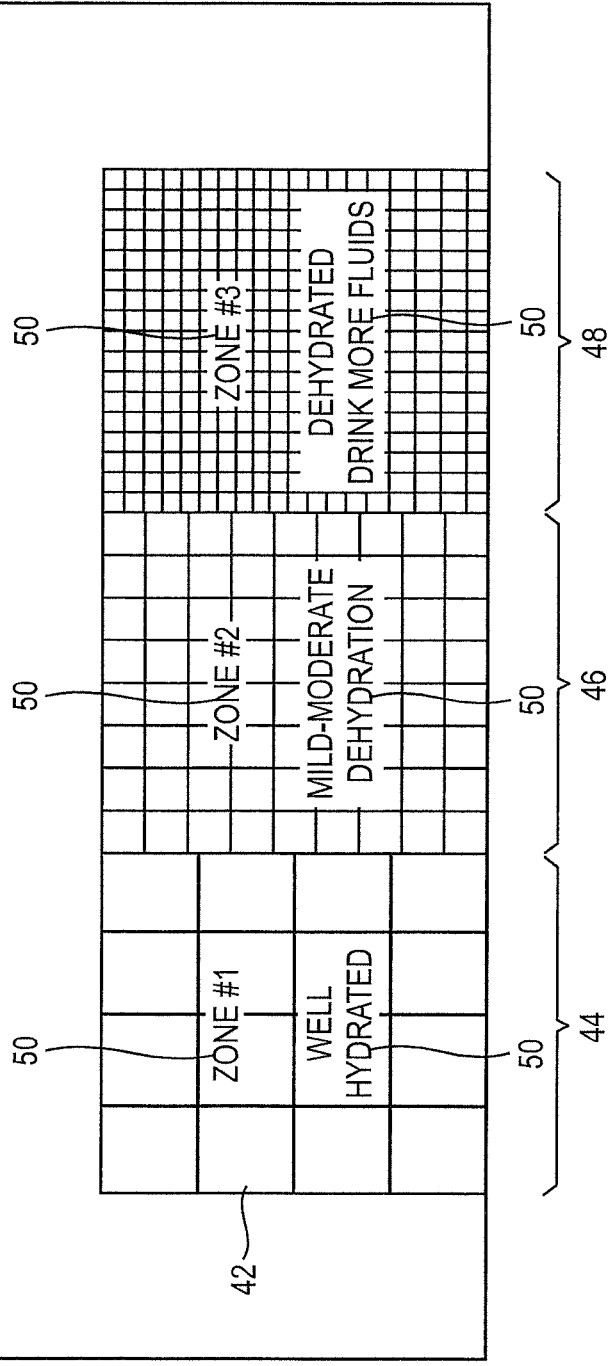
FIG. 4 is a top view of a placard including a second color scale.

FIG. 4 illustrates an example of the placard 40. The second color scale 42 includes a plurality of color regions 44, 46 and 48 and hydration level indicators 50. The layout of the color regions 44, 46 and 48 and hydration level indicators 50 is identical to the color regions 24, 26 and 28 and hydration level indicators 30 included on the nonabsorbent urine analysis device 10. The identical layout of the color scale of the placard 40 and the color scale of the nonabsorbent urine analysis device 10 helps the individual understand how the placard 40 is related to the nonabsorbent analysis device 10. This increases the likelihood that the individual will accurately assess his or her hydration level. However, it is not required that the color scales of the placard 40 and the nonabsorbent urine analysis device 10 are identical. In one embodiment, the hydration level indicators 30 on the nonabsorbent urine analysis device 10 may simply be a number assigned to each color region, whereas the hydration level indicators 50 on the placard 40 may include both numbers and text describing the hydration level corresponding to each number. As shown in FIG. 4, the placard 40 may also include written instructions describing how to use the nonabsorbent analysis device 10 to determine one's hydration level.

The placard 40 may include an adhesive backing for bonding the placard 40 to the wall. The placard 40 can be made of paper, plastic or any other suitable material. The placard 40 may be water-resistant, but does not have to be water-resistant because it is not subject to intermittent flows of water like the nonabsorbent urine analysis device 10 applied to the urinal.

Figure 5:
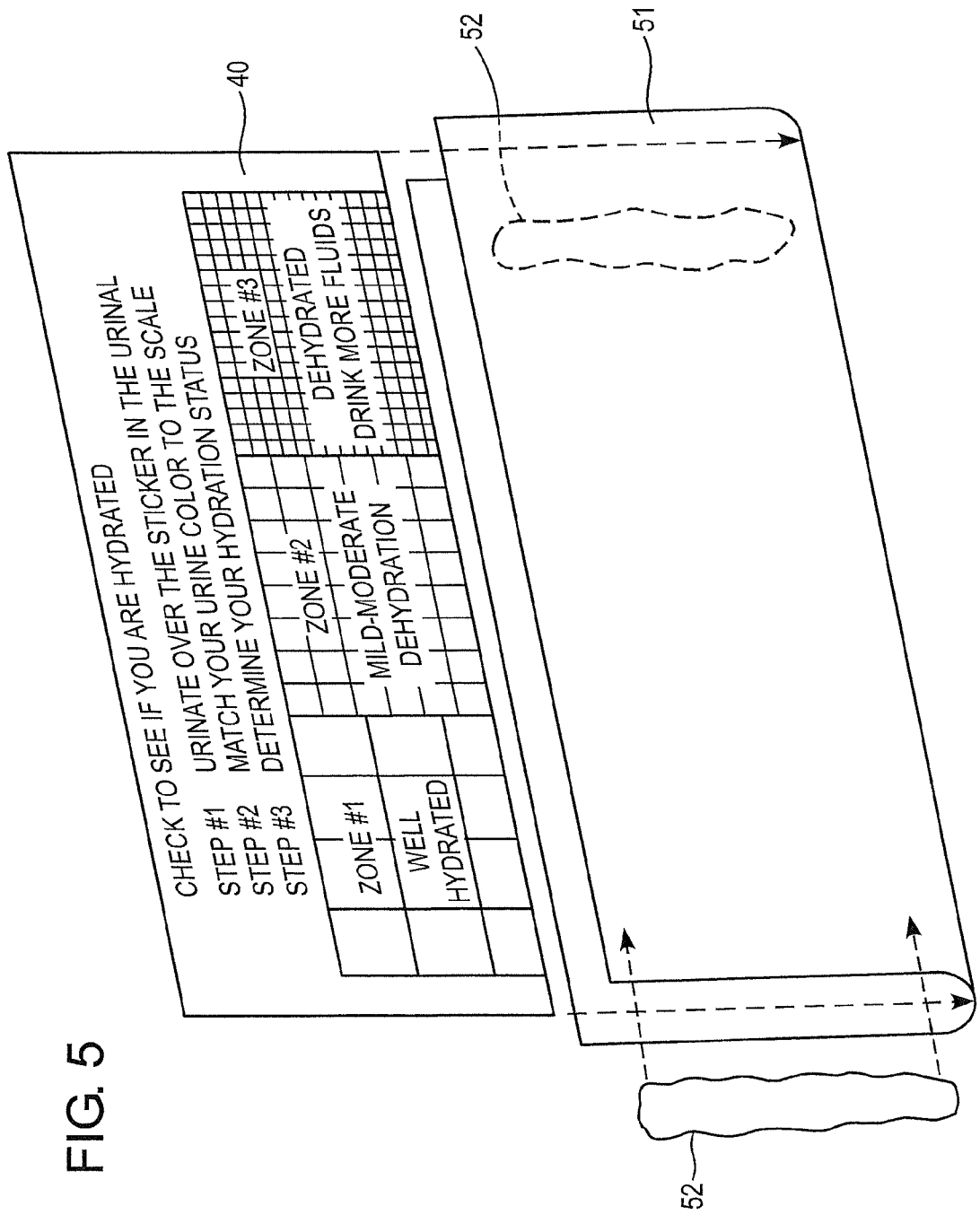
FIG. 5 illustrates a clear plastic sheath for holding the placard.

FIG. 5 illustrates a clear plastic sleeve 51 for holding the placard 40. The clear plastic sleeve 51 can be mounted on the wall above the urinal 34. Double-sided adhesive tape strips 52 may be used to adhere the clear plastic sleeve 51 to the wall. The clear plastic sleeve 51 may possess a U-shape to prevent the placard 40 from falling out of the bottom of the clear plastic sleeve 51. The clear plastic 51 can be mounted on the wall at eye-level so that an individual using the urinal 34 has a relatively close view of the placard 40.

In one embodiment, a second nonabsorbent urine analysis device 10 is employed as the placard 40. In such an embodiment, one nonabsorbent urine analysis device 10 is adhered to the urinal and another nonabsorbent urine analysis device 10 is adhered to the wall.

Figure 6:
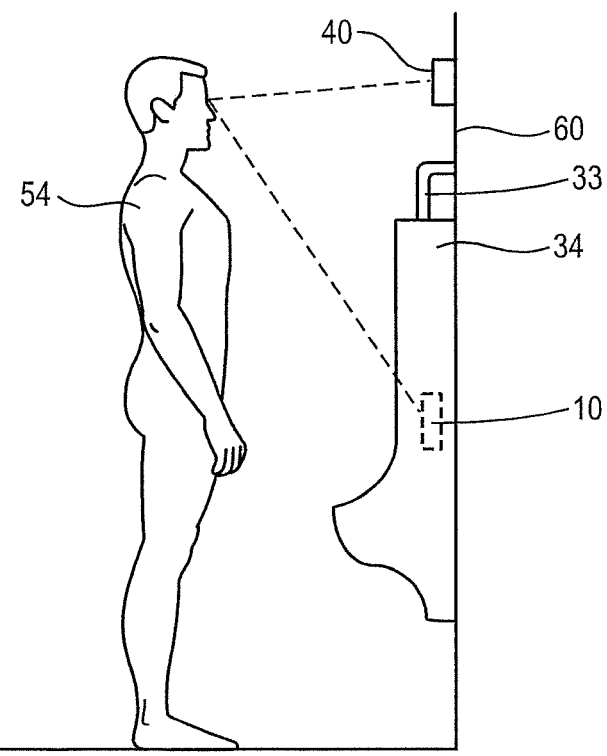
FIG. 6 a side view of an individual using the nonabsorbent urine analysis device and the placard.
Figure 7:
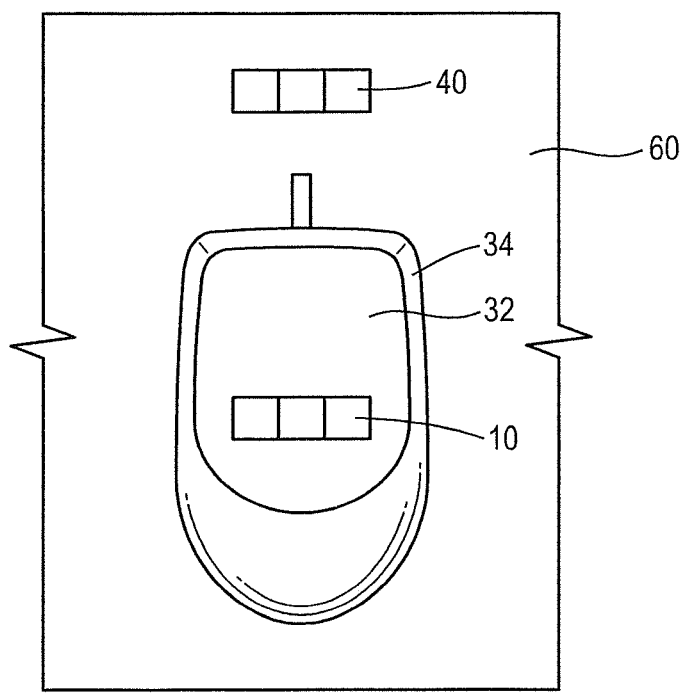
FIG. 7 is a front view of the nonabsorbent urine analysis device and the placard illustrated in FIG. 6.

FIG. 6 illustrates a side view of an individual 54 using the placard 40 and the nonabsorbent urine analysis device 10. The individual 54 initially stands in front of the urinal 34 attached to the wall 60, and then urinates on the nonabsorbent urine analysis device 10 adhered to the urinal 34. As the urine flows over the nonabsorbent urine analysis device 10, the individual 54 visually compares the urine color to the color scale 14. The individual 54 subsequently identifies a color on the color scale 14 which most closely matches the urine color. The individual 54 next determines the hydration level by reading the hydration level indicator 30 on the nonabsorbent urine analysis device 10. If the individual 54 cannot read the hydration level indicator 30 because it is too far away or obstructed from view, or if the individual 54 simply wants to confirm his reading of the nonabsorbent urine analysis device 10, the individual 54 looks to the placard 40. The placard 40 is placed at eye-level so that it is close to the face of the individual 54 using the urinal 34. The individual 54 finds the matched color on the second color scale 42. The individual 54 then determines and/or confirms the hydration level by reading the hydration level indicator 50 on the placard 40 that corresponds to the matched color. The placard 40 thus helps the individual 54 assess the urine color. FIG. 7 illustrates a front view of the urinal 34 illustrated in FIG. 6, with the individual 54 being omitted.

In one embodiment, the hydration level indicators 30 on the nonabsorbent urine analysis device 10 are simply numbers and do not convey any meaningful information about the hydration level corresponding to the different colors. In this embodiment, the hydration level indicators 50 of the placard 40 include the same numbers as the nonabsorbent urine analysis device 10, and additionally, a written explanation of the hydration level corresponding to each of the different numbers. The individual 54 reads the number from the nonabsorbent urine analysis device 10, and then finds that same number on the placard 40 to determine the hydration level. In this embodiment, the placard 40 may not include the second color scale 42.

In one embodiment, the placard 40 is not used in combination with the nonabsorbent urine analysis device 10. The placard 40 is placed on the wall above the urinal 34, and the user compares the urine color directly to the second color scale 42 on the placard 40 without referencing the nonabsorbent urine analysis device 10. In such an embodiment, there may be no nonabsorbent urine analysis device 10 adhered to the urinal 34.

Figure 8:
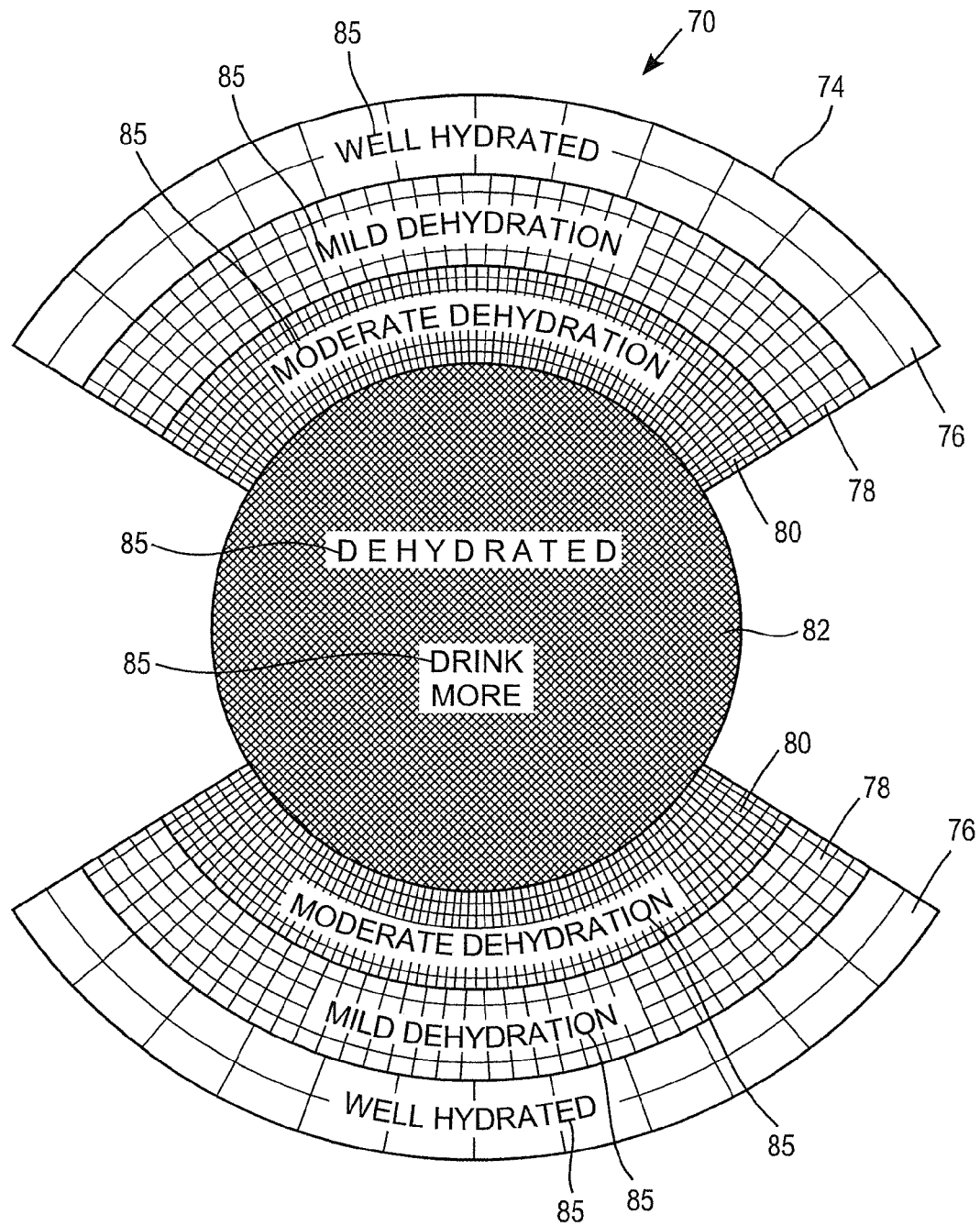
FIG. 8 is a view of another embodiment of the nonabsorbent urine analysis device.

FIG. 8 illustrates another embodiment of the nonabsorbent urine analysis device 70. The nonabsorbent urine analysis device 70 possesses the same layers of material as the nonabsorbent urine analysis device 10 described above. The nonabsorbent urine analysis device 70 includes a color scale 74 possessing a plurality of concentrically-arranged color regions 76, 78, 80 and 82. The colors become darker as one moves closer to the center of the nonabsorbent urine analysis device 70. The darker colors are depicted in FIG. 8 with denser cross hatching. The darkest color region 82 is located at the center of the nonabsorbent urine analysis device 70, and the lightest color region 76 is located at the radially outermost portion of the nonabsorbent urine analysis device 70. The lightest color region 76 may be a light shade of yellow and the darkest color region 82 may be a dark shade of yellow or a brownish-green color.

Each color region 76, 78, 80 and 82 may possess a single color. Alternatively, the color scale 74 may progressively change from lighter colors to darker colors so that there is not a distinct color transition between each of the different color regions 76, 78, 80 and 82. That is, each color blends into an adjacent color. In such an embodiment, each color region 76, 78, 80 and 82 may include multiple shades of color.

Each of the color regions 76, 78, 80 and 82 corresponds to a different level of hydration such as euhydration, mild dehydration, moderate dehydration and severe dehydration. Each of the color regions 76, 78, 80 and 82 includes a hydration level indicator 85 that helps an individual determine the hydration level. The hydration level indicator 85 can include words, numbers and/or a graphic.

The concentric arrangement of the color regions 76, 78, 80 and 82 may be advantageous when the nonabsorbent urine analysis device 70 is applied to a lower portion of the urinal near the drain, or to the top surface of a urinal deodorizer block (e.g., a urinal cake). The individual can apply the stream of urine to the center of the nonabsorbent urine analysis device 70 on the color region 82. The stream of urine radially disperses over the nonabsorbent urine analysis device 70 thereby flowing over the other color regions 76, 78 and 80. The individual can then identify the color region which most closely matches the urine color, and determine his or her hydration level accordingly. A white background or empty space may separate some or all of the color regions 76, 78, 80 and 82 to help the user compare the urine color to the color regions 76, 78, 80 and 82.

Figure 9:
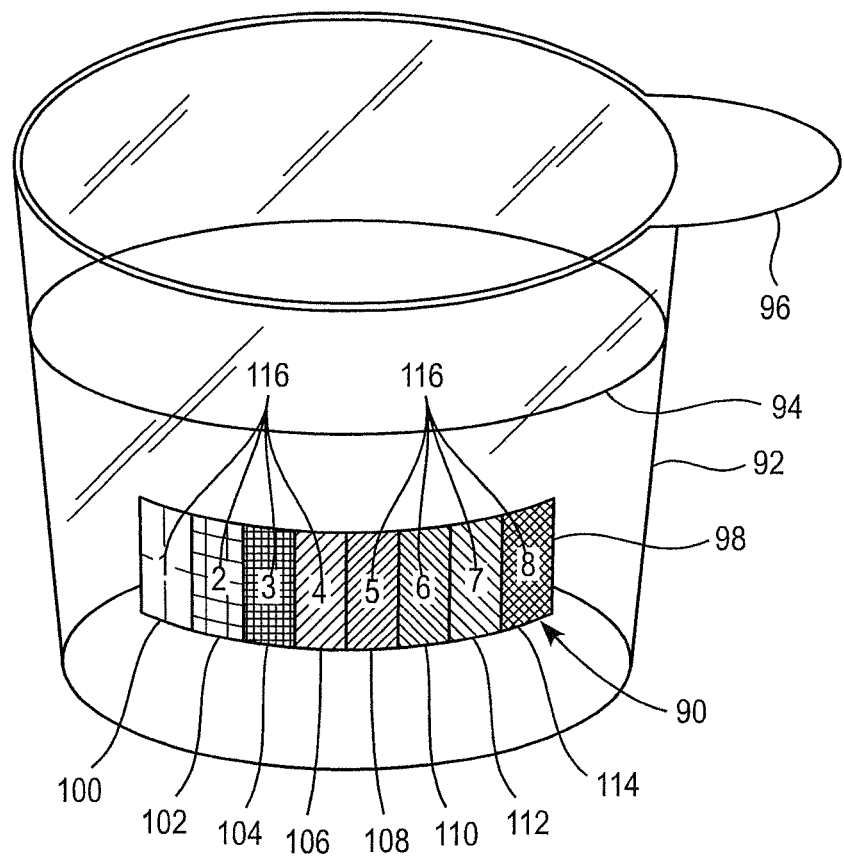
FIG. 9 is a view of another embodiment of the nonabsorbent urine analysis device.

The nonabsorbent urine analysis device can be applied to urine receptacles besides a urinal or toilet. FIG. 9 illustrates another embodiment of the nonabsorbent urine analysis device 90 adhered to the exterior of a transparent cup 92 filled will urine 94. The transparent cup 92 includes a handle 96 so that an individual can hold the transparent cup 92 while urinating into the transparent cup 92. Positioning the nonabsorbent urine analysis device 90 on the transparent cup 92 may facilitate female use of the nonabsorbent urine analysis device 90. A female individual's view of her urine stream may be obstructed during urination. The transparent cup 92 allows the female individual to first collect the urine sample, and then hold the urine sample at eye-level to assess the urine color with the nonabsorbent urine analysis device 90.

The nonabsorbent urine analysis device 90 may possess the same layers of material as the nonabsorbent urine analysis device 10 described above. The nonabsorbent urine analysis device 90 may lack a water-resistant layer because it is not directly exposed to urine or water. The nonabsorbent urine analysis device 90 includes a color scale 98 possessing a plurality of linearly-arranged color regions 100, 102, 104, 106, 108, 110, 112 and 114. The colors regions 100-114 darken form left to right in FIG. 9. The lightest color region 100 may be a light shade of yellow and the darkest color region 114 may be a dark shade of yellow or brownish-green color.

Each of the color regions 100-114 may possess a single color, or alternatively, the color scale 90 may progressively change from lighter colors to darker colors so that there is not a distinct color transition between each of the different color regions 100-114. Each of the color regions 100-114 corresponds to a different level of hydration, and includes a hydration level indicator 116 that helps an individual determine the hydration level. The hydration level indicator 116 can include words, numbers and/or a graphic. The nonabsorbent urine analysis device 90 may be used in combination with a placard which provides more detailed information about the hydration level corresponding to each color.

The different embodiments of the nonabsorbent urine analysis device illustrated by way of the drawings possess a generally rectangular or circular shape. The nonabsorbent urine analysis device can also be shaped to resemble a square, ellipse, pentagon or any other polygon. The nonabsorbent urine analysis device can also have an amorphous shape.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A nonabsorbent urine analysis device to be adhered to a urine receptacle for determining a hydration level based on urine color, the nonabsorbent urine analysis device comprising:
   a base possessing a front side and a back side;
   a color scale applied to the front side of the base, the color scale including at least a plurality of shades of yellow, each of the shades of yellow corresponding to a hydration level based on urine color; and
   a water-resistant adhesive applied to the back side of the base, the water-resistant adhesive being configured to adhere the base to the urine receptacle, wherein the urine analysis device is nonabsorbent.

2. The nonabsorbent urine analysis device of claim 1, further comprising a plurality of hydration level indicators applied to the front side of the base, each hydration level indicator being positioned adjacent to and/or overlapping at least one of the shades of yellow.

3. The nonabsorbent urine analysis device of claim 2, wherein each hydration level indicator includes text and/or a graphic describing the hydration level corresponding to at least one of the shades of yellow.

4. The nonabsorbent urine analysis device of claim 2, further comprising a transparent, water-resistant layer covering at least the color scale and the plurality of hydration level indicators.

5. The nonabsorbent urine analysis device of claim 1, wherein the color scale progressively changes from lighter shades of yellow to darker shades of yellow so that each shade of yellow blends into an adjacent shade of yellow.

6. The nonabsorbent urine analysis device of claim 1, wherein the plurality of shades of yellow are linearly arranged from lightest to darkest.

7. The nonabsorbent urine analysis device of claim 6, a first end of the color scale including the lightest shade of yellow and a second end of the color scale including a brownish-green color.

8. The nonabsorbent urine analysis device of claim 1, wherein the color scale possesses a circular shape, and the plurality of shades of yellow are arranged concentrically with the darkest shade of yellow being radially inward of the lightest shade of yellow.

9. A method for determining a hydration level based on urine color comprising:
applying a stream of urine to a water-resistant color scale adhered to a urine receptacle so that the urine flows over the water-resistant color scale;
visually comparing the urine color to a plurality of colors included on the water-resistant color scale while the urine flows over the water-resistant color scale;
identifying a color included on the water-resistant color scale which most closely matches the urine color; and
determining the hydration level by referencing a hydration level indicator corresponding to the identified color.

10. The method of claim 9, wherein the hydration level indicator is included on the water-resistant color scale adjacent to and/or overlapping the identified color.

11. The method of claim 9, wherein the hydration level indicator includes text and/or a graphic describing the hydration level corresponding to the identified color.

12. The method of claim 9, wherein the plurality of colors of the water-resistant color scale include a plurality of shades of yellow arranged from lightest to darkest.

13. The method of claim 9, wherein a first end of the water-resistant color scale includes a yellow color and a second end of the water-resistant color scale includes a brownish-green color.

14. The method of claim 9, wherein the hydration level indicator is included on a second color scale positioned exteriorly of the urine receptacle.

15. The method of claim 14, wherein the water-resistant color scale adhered to the urine receptacle and the second color scale positioned exteriorly of the urine receptacle each include an identical arrangement of colors and hydration level indicators.

16. The method of claim 14, wherein the urine receptacle is a urinal mounted on a wall, and the second color scale is positioned above the urinal on the wall.

17. A urine analysis system comprising:
a urinal including a urine reception surface;
a first color scale adhered to the urine reception surface by a water-resistant adhesive, the first color scale being water-resistant and including a plurality of shades of yellow;
a second color scale positioned exteriorly of the urinal and including a plurality of shades of yellow arranged from lightest to darkest; and
the second color scale including a plurality of hydration level indicators positioned adjacent to and/or overlapping at least one of the shades of yellow on the second color scale.

18. The urine analysis system of claim 17, wherein the urinal is mounted on a wall, and the second color scale is positioned on the wall above the urinal.

19. The urine analysis system of claim 17, wherein the first color scale includes an identical arrangement of shades of yellow and hydration level indicators as the second color scale.

20. The urine analysis system of claim 17, wherein the hydration level indicator includes text and/or a graphic describing the hydration level corresponding to at least one of the shades of yellow on the second color scale.

* * * * *